United States Patent
Harju et al.

(10) Patent No.: US 6,842,241 B2
(45) Date of Patent: Jan. 11, 2005

(54) METHOD FOR CHECKING THE OPERATION OF AN OPTICAL MEASURING DEVICE AND CHECKING DEVICE

(75) Inventors: Raimo Harju, Turku (FI); Sanna Tauluvuori, Turku (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 10/233,676

(22) Filed: Sep. 4, 2002

(65) Prior Publication Data

US 2003/0086085 A1 May 8, 2003

(30) Foreign Application Priority Data

Sep. 4, 2001 (FI) .............................................. 20011756

(51) Int. Cl.⁷ .............................. G01J 1/10; G01B 9/08
(52) U.S. Cl. ..................................... 356/243.1; 356/392
(58) Field of Search ........................... 356/243.1–243.8, 356/244–246, 388, 392; 422/61, 73

(56) References Cited

U.S. PATENT DOCUMENTS

| | | | | |
|---|---|---|---|---|
| 4,431,924 A | * | 2/1984 | Suovaniemi et al. | 250/566 |
| 5,157,455 A | * | 10/1992 | Macri et al. | 356/243.8 |
| 5,183,761 A | | 2/1993 | Freeman et al. | 436/8 |
| 5,234,665 A | * | 8/1993 | Ohta et al. | 422/73 |
| 5,258,308 A | * | 11/1993 | Freeman et al. | 436/8 |
| RE34,841 E | * | 1/1995 | Suovaniemi et al. | 356/244 |
| 5,492,673 A | * | 2/1996 | Curtis et al. | 422/61 |
| 5,770,860 A | * | 6/1998 | Franzen | 250/288 |
| 6,157,446 A | * | 12/2000 | Baer et al. | 356/244 |
| 6,348,965 B1 | | 2/2002 | Palladino et al. | 356/243.1 |
| 6,519,032 B1 | * | 2/2003 | Kuebler et al. | 356/337 |

FOREIGN PATENT DOCUMENTS

| | | |
|---|---|---|
| EP | 1124128 A | 8/2001 |
| JP | 1142440 A | 6/1989 |
| JP | 07/010594 A | 1/1995 |
| WO | 96/07888 A | 3/1996 |
| WO | 96/32631 A | 10/1996 |
| WO | 00/08440 A | 2/2000 |

* cited by examiner

Primary Examiner—Michael P. Stafira
(74) Attorney, Agent, or Firm—Kubovcik & Kubovcik

(57) ABSTRACT

A method for checking the operation of a laboratory instrument used in biochemistry by means of an individual test plate (10) by comparing measured values of sample units (20, 21) placed in the wells (12) of the frame plate (11) to previously known measured values verified by a reference device. The sample unit (20) placed in the frame plate (11) of the test plate (10) is a teflon plastic cup (22) provided with an aluminum cover (23), the sample material (24) in powdery form being placed in said cup, or an optical filter (21), which is locked in place by means of a locking spring ring (25).

10 Claims, 3 Drawing Sheets

METHOD FOR CHECKING THE OPERATION OF AN OPTICAL MEASURING DEVICE AND CHECKING DEVICE

SUBJECT OF THE INVENTION

The present invention relates to a method for checking the operation of an optical measuring device, such as a laboratory instrument used in biochemistry, by means of a checking device, such as a test plate, according to the method a test plate is formed for the measuring device by placing in the wells of a plate corresponding to a micro titer plate different sample units whose verified measured values are known, and that the checking of the operation of the measuring device is accomplished by measuring the sample units placed in the wells of the aforesaid plate and comparing the measurement results obtained to previously known measured values verified by means of a reference device.

In biochemistry, laboratory instrument measuring devices are used to carry out e.g. fluorescence measurements and/or luminescence measurements and/or photometric measurements and/or similar laboratory measurements.

The invention relates to in particular to checking the operation of optical plate readers that use sample plates containing a plurality of sample wells. The sample plate used in connection with the invention may be almost any kind of plate, but sample wells like the commonly used so-called micro titer plates are well applicable in the invention. Prior-art micro titer plates have a large number of sample wells disposed in a matrix form, the number of wells being traditionally 96. However, micro titer plates containing 384, 864 or 1536 wells are also common. The size of the micro titer plate has been standardized so that its external dimensions are always the same, but as the number of sample wells is increased, the well size is naturally smaller.

PRIOR ART

A prior-art device for checking the operation of an optical plate reader is a ceramic body the size of a micro titer plate in external dimensions, i.e. a standard plate with fluorescent material sintered inside it. This fluorescent compound in different concentrations is placed at the locations on the standard plate corresponding to the locations of sample wells in the micro titer plate. Thus, one ceramic standard plate can be used for calibrating the intensity of a measuring device at a wavelength corresponding to the fluorescent compound. For the calibration of other wavelengths of the measuring device, separate standard plates provided in a corresponding manner with sintered fluorescent material corresponding to another wavelength are needed.

Another prior-art device for checking the operation of an optical plate reader is a plate the size of a micro titer plate, having a plurality of filters placed side by side for the calibration of a photometric device. Prior-art devices have also been presented in the documents WO A 00/08440 (G01N 21/27), EP A 1124128 (G01N 21/64), U.S. Pat. No. 5,183,761 (G01N 21/00), WO A 96/32631 (G01N 21/27), WO A 96/07888 (G01N 21/64), U.S. Pat. No. 6,348,965 (G01J 1/10). 1.

Prior-art checking devices, however, have the drawback that they can generally only be used for checking one measuring method of a measuring device. Therefore, they are very unversatile, which is why it is necessary to use several plates to check e.g. the operation of a multi-label device.

OBJECT OF THE INVENTION

The object of the invention is to achieve a method that can be used to create an effective system for checking the functionality of measuring devices used e.g. for various determinations and also of devices using several different measuring methods.

FEATURES CHARACTERISTIC OF THE METHOD OF THE INVENTION

The method of the invention is characterized in that an individual test plate is formed for each measuring device, in the aforesaid test plate, sample units are placed by means of which the reliability of the measuring device can be tested by the measuring methods used by the measuring device, such as e.g. fluorescence, luminescence and photometric determinations, the aforesaid test plate is marked with an identifier, such as e.g. a serial number, identifying the measuring device, and that the user of the aforesaid measuring device checks the operation of the measuring device by performing a measurement on the device-specific individual test plate and comparing the measurement results obtained to previously known measurement values for the test plate, verified by a reference device.

For the test plate, sample units best corresponding to the measuring methods used by the measuring device are selected. Thus, the fluorescent materials selected for use in the sample units in a test plate for a multi-label measuring device are different fluorescent substances such that the measurement result produced by them corresponds e.g. to fluorescence, luminescence and photometric determinations.

By the method of the invention, it is also possible to check the operation of so-called multi-label measuring devices quickly and effectively, a task that has been very difficult to perform by prior-art methods.

DEVICE OF THE INVENTION

The invention also concerns a device, such as a test plate, for checking the operation of an optical measuring device, such as a laboratory instrument used in biochemistry, at least one previously verified measurement value for said device being known, which checking device comprises a frame plate, which preferably is the size of a micro titer plate, the frame plate is provided with wells or similar mounting points for sample units, the sample units are solid bodies that can be fixedly mounted in the wells or similar mounting points of the frame plate.

FEATURES CHARACTERISTIC OF THE DEVICE OF THE INVENTION

The device of the invention is characterized in that the sample unit to be mounted in a well in the frame plate of the said checking device is a cup, inside which the sample material is placed, and that the sample unit comprises a cover for closing the cup.

EMBODIMENTS OF THE DEVICE OF THE INVENTION

A preferred embodiment of the checking device of the invention is characterized in that the cup of the sample unit of said checking device is made of a material as neutral as possible in regard of measurement, such as teflon plastic or a ceramic material, the cup contains a fluorescent substance, preferably in the form of powder, the cover of the cup is made of a material as stable as possible, such as black anodized aluminum, the cup is so placed in the frame plate of the checking device that optical measurement takes place through the bottom of the cup, and that the cup is placed in the frame plate of the checking device with its bottom upward when optical measurement is performed from above the frame plate through the bottom of the cup.

A second preferred embodiment of the checking device of the invention is characterized in that the sample material in the cup of the sample unit of the aforesaid checking device is fluorescent powder as such or diluted with non-fluorescent powder.

A third preferred embodiment of the checking device of the invention is characterized in that the sample material in the cup of the sample unit of the aforesaid checking device consists of fluorescent powder to which a liquid producing luminescence or similar material has been added.

A fourth preferred embodiment of the checking device of the invention is characterized in that the sample unit to be mounted in a well in the frame plate of the aforesaid checking device is an optical filter, which preferably consists of a metal-coated quartz plate.

A fifth preferred embodiment of the checking device of the invention is characterized in that the frame plate of the aforesaid checking device is preferably made of black plastic, that the frame plate contains preferably 96 wells of circular cross-section, and that the sample units fitted to the wells and fixedly mounted in them have a corresponding round shape.

A sixth preferred embodiment of the checking device of the invention is characterized in that placed in the wells of the frame plate of the aforesaid checking device are sample units used for the checking of two or more measuring methods, e.g. fluorescence and/or luminescence and/or photometric measuring units.

An seventh preferred embodiment of the checking device of the invention is characterized in that one or more wells in the frame plate of the aforesaid checking device have an aperture in their bottom so that a through hole exists in the frame plate in the region of the aperture, at least one cup of the sample unit is placed with the cover upward in a well with an aperture in its bottom, thus permitting an optical measurement to be performed through the bottom of the cup from below the frame plate via the aforesaid aperture, at least one optical filter of the sample unit is placed in a well with an aperture in its bottom, permitting an optical measurement penetrating said filter to be performed from either side of the frame plate.

A eighth preferred embodiment of the checking device of the invention is characterized in that the sample unit, which comprises a sample cup or which is an optical filter, is placed on the bottom of a well in the frame plate of the checking device, and that, to lock the sample unit in place, the well in the frame plate is provided with a locking ring, such as a spring ring, placed above the sample unit.

As the method and checking device of the invention are efficient and economical, it is possible to impose on the laboratory personnel using the measuring equipment an obligation to monitor the functionality and accuracy of their measuring devices by carrying out a check using an individual test plate provided together with the measuring device. If a measuring device delivered earlier was not accompanied by an individual test plate, then the test plate can be manufactured and delivered to the client even afterwards. Thus, the method and test plate of the invention supercede the very difficult checking operations performed using standard and adjustment solutions by the users of measuring devices.

Likewise, in connection with maintenance of the measuring device it is easy to verify using the test plate that the measuring device meets the requirements it is subject to. If it is detected during the check that the measuring device has to be readjusted, then the fine adjustment of the measuring device is still generally carried out using standard and adjustment solutions.

In connection with optical plate readers it is advantageous to use a 96-pit test plate having main dimensions corresponding to those of a 96-well micro titer plate. In this way, test plates that fit even older measuring devices can be easily formed afterwards. It is therefore possible to place any sample units in the frame of the test plate as they all fit into the wells or pits of the plate. The sample units are mainly buttons of identical size, consisting of cups closeable by a cover and containing powder or e.g. of quartz plate filters. Each button produces an optical measurement result, the value of which is compared to a previously measured measurement value for the button that has been verified by means of a reference device.

Depending on the measuring device, the test plate contains different sample buttons fixedly placed in the wells or pits of the test plate. Fluorescent sample buttons contain powdery fluorescent material, e.g. $Y_2O_3$:Eu in a teflon cup closed by a black anodized aluminum cover or plug. If the measurement is performed from above the test plate through the bottom of the sample cup, then the buttons are placed upside down in the pits of the test plate, i.e. with the bottom of the sample cup upward and the aluminum plug against the bottom of the well. On the other hand, if the measuring device is of a type that performs the optical measurement from below the sample plate, then the sample buttons are placed the right way round, i.e. with the aluminum plug upward in the wells of the test plate. In this case, the measurement is performed from below via the aperture in the bottom of the well of the sample plate through the bottom of the sample cup. The sample buttons are locked in place in the wells of the test plate by means of locking spring rings that are pressed against the walls of the wells and are thus locked in place, said locking springs being placed onto the sample buttons in the wells.

For each label there is a separate button, whose spectral properties are compatible with the properties of the measuring device in question that are to be tested. To reach suitable signal levels, some fluorescent materials have to be diluted with non-fluorescent powdery materials, such as e.g. $Al_2O_3$, $TiO_2$ and active carbon. As a void BLANK sample, an empty teflon cup with an aluminum plug is used.

In the luminescence buttons that are placed in the test plate when necessary, e.g. the same powdery fluorescent material is used as in the fluorescence buttons, but it is activated by additionally pipetting into the teflon cup a liquid radioactive compound, such as $^{14}C$ palmitinic acid. Before the luminescence button is closed with an aluminum cover, the dissolvent of the pipetted liquid substance is evaporated away, thus turning the luminescence sample into a solid state.

In addition to sample buttons as described above, it is also possible to mount one or more neutral density filters in those wells of the test plate that have an aperture in the bottom. The neutral density filter is e.g. a disc cut from a quartz plate, thus forming a photometric standard.

EMBODIMENT EXAMPLES

In the following, the invention will be described by the aid of example with reference to the attached drawings, wherein List of Figures FIG. 1 presents a test plate according to the invention in top view.

FIG. 2 corresponds to FIG. 1, showing a test plate with sample unit positions indicated.

FIG. 3 presents a vertical section of a detail of the test plate in FIG. 1 and of sample units to be mounted in the wells of the test plate.

FIG. 4 presents a vertical section of a detail of the test plate in FIG. 2, with sample units mounted in it.

FIG. 5 presents a block diagram showing the steps of the method according to the invention.

DESCRIPTION OF THE FIGURES

In the test plate 10 in FIG. 2, different sample units 20 and 21 have been placed in several rows in the wells 12 of the frame plate 11. In the test plate 10, the sample units 20 and 21 are grouped e.g. so that sample units 20a are fluorescence samples, sample units 20b are long-lasting photoluminescence samples and sample units 20c are luminescence samples. All the above-mentioned sample units 20a–20c contain a known fluorescent material, which according to this embodiment is placed in powdery form in a teflon cup, which is closed with an aluminum cover.

The fluorescent material to be used in each sample unit 20a–20c is selected separately so that each sample unit 20a–20c corresponds to a measuring method used by the measuring device to be tested. Thus, the test measurement produces a measurement result that makes it possible to estimate whether the device is operational with the measuring method used. For example, a measuring device that uses a time-resolution measuring method can be tested by using a long-lasting photoluminescence sample unit 20c.

Figure 1:
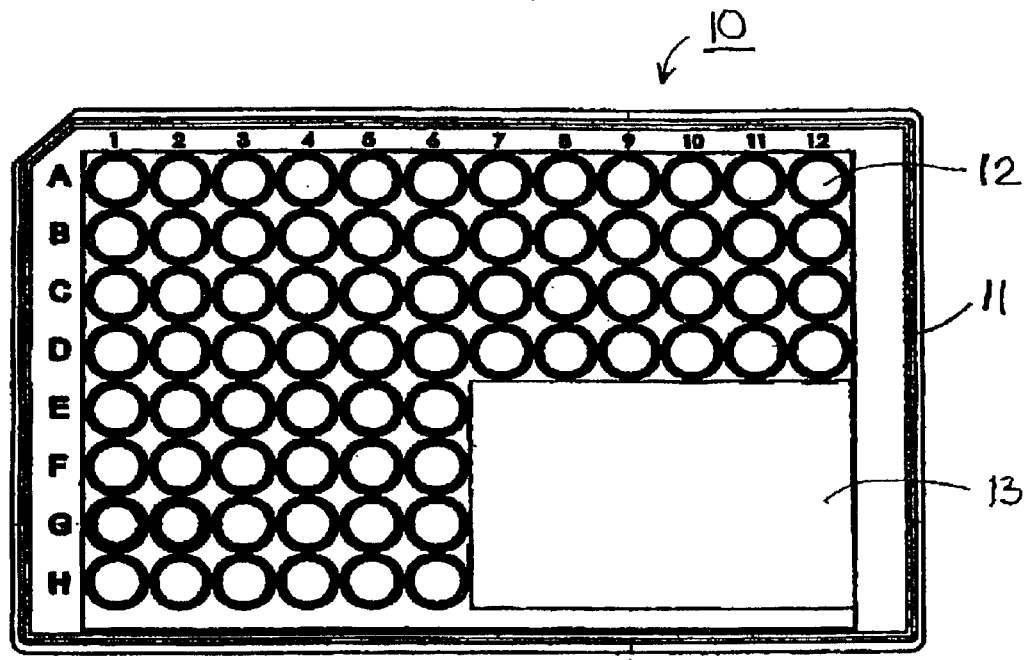
FIG. 1 presents a top view of a test plate 10 according to the invention, comprising a frame plate 11 provided with wells 12, in which are placed sample units consisting of sample buttons and/or filter plates. In the embodiment of the test plate 10 presented in FIG. 1, the frame plate 11 it is also provided with a cover plate 13, which covers most of the wells 12. The cover plate can be used e.g. as a name plate or as an identifier of the sample plate 10.
Figure 2:
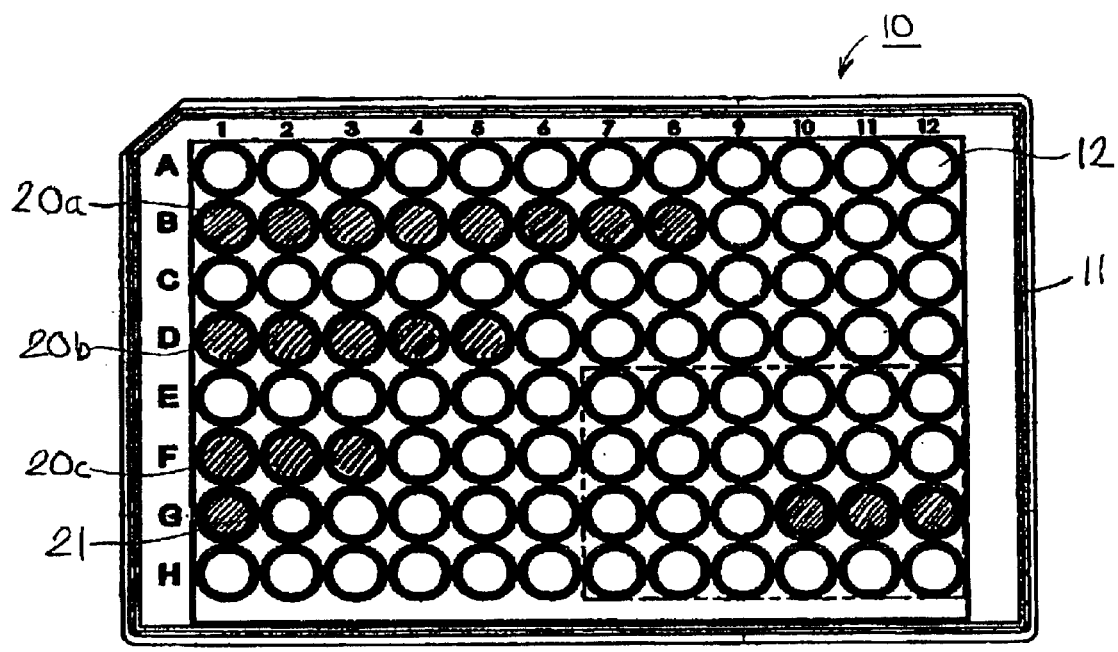
Figure 3:
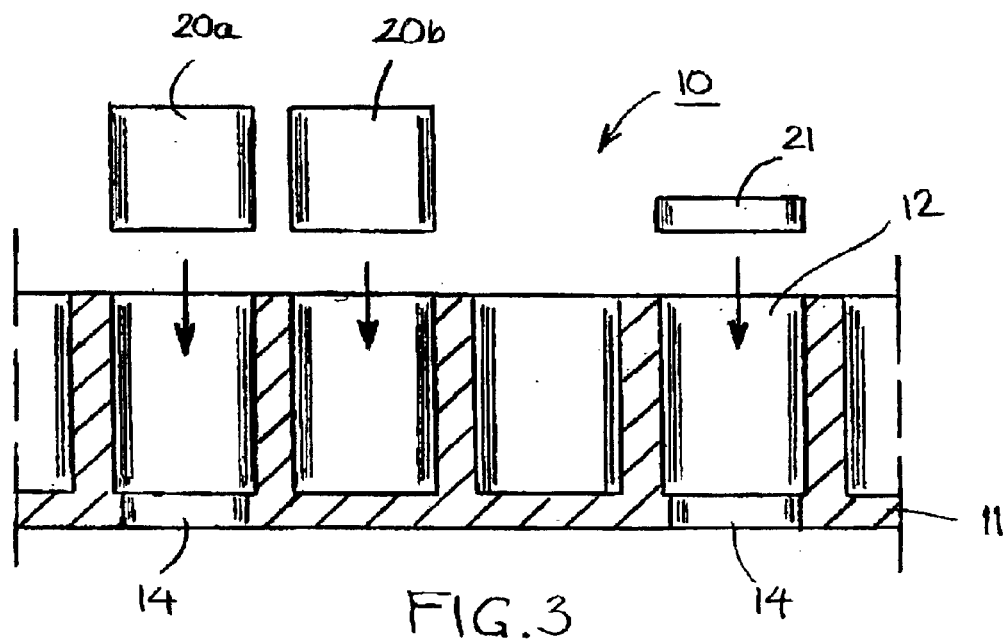

FIG. 3 presents a vertical section of a detail of the test plate 10 in FIG. 1, showing a number of wells 12 formed in the frame plate 11. The frame plate 11 is made of e.g. colorless or black plastic. Some of the wells 12 in the frame plate 11 have a solid bottom, whereas some of the wells 12 have an aperture 14 in the bottom. A sample 20 in a well 12 with a solid bottom can only be measured from above the frame plate 11. On the other hand, if the well 12 has an aperture 14 in the bottom, then the sample 20 can be measured from below the frame plate 11 as well.

Figure 4:
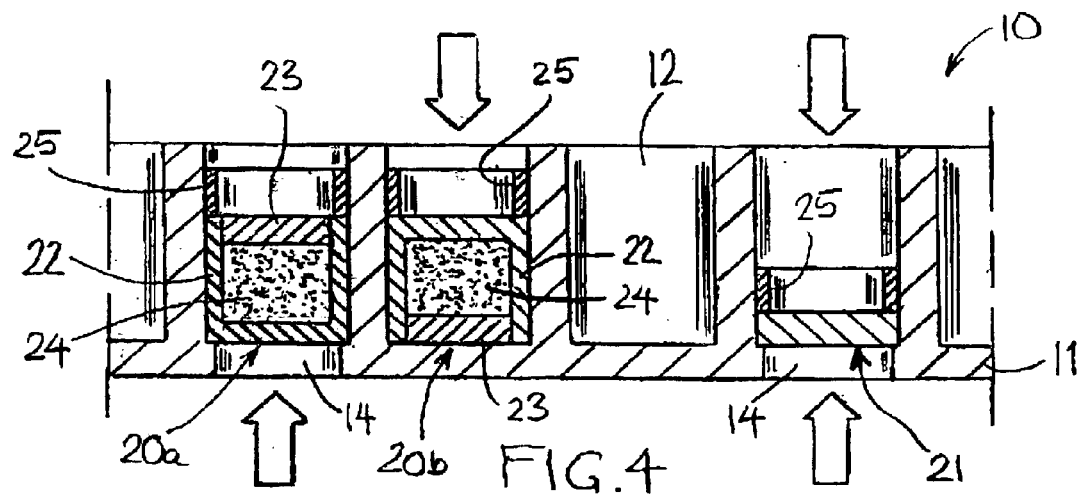
FIG. 4 illustrates the structure of the cups in greater detail. In the embodiment of the test plate 10 presented in FIG. 2, besides the sample units 20a–20c containing fluorescent material, in one 12 of the wells of the frame plate 11 is placed a photometric standard 21, which is a neutral density filter cut from a quartz plate.
Figure 5:
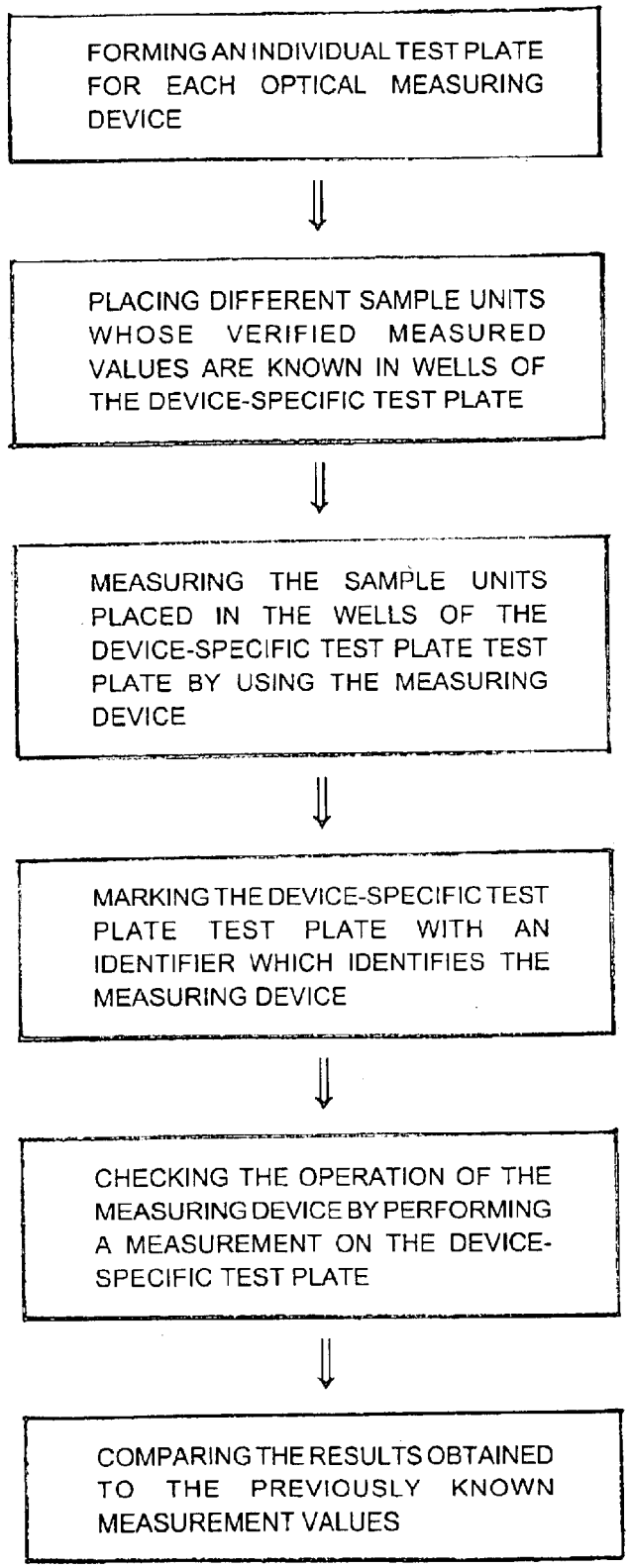

FIG. 4 presents an embodiment of the test plate 10 in which different sample units 20 and 21 have been placed in the wells 12 of the frame plate 11. From this vertical sectional view it can be seen that the sample units 20a and 20b are cups 22 closed with a cover 23, the cup part 22 being preferably made of teflon and the cover part 23 of black anodized aluminum. The cups 22 have been filled with powdery fluorescent material 24 and the tightly fitted cover 23 has been pressed into the teflon cup 22 so that it sits tightly over the powder 14. Thus, the cup 22, the powder 24 placed in it and the tight cover 23 form a sample unit button 20 in the test plate 10, and this button is locked in place in the well 12 of the frame plate 11 by means of a locking spring ring 25.

As can be seen from FIG. 4, the sample unit button 20 can be placed in the well 12 of the frame plate 11 either the right way round or upside down. In FIG. 4, the teflon cup 22 of sample unit 20a has been placed the right way round with the aluminum cover 23 upward, because an optical measurement can be performed in the direction of the arrow shown in the figure, from below the test plate 10 via the aperture 14 in the bottom of the well 12 of the frame plate 11 through the bottom of the teflon cup 22. By contrast, the teflon cup 22 of sample unit 20b in FIG. 4 has been placed upside down with the aluminum cover 23 downward, because the well 12 of the frame plate 11 has a solid bottom and a optical measurement can only be performed in the direction of the arrow shown in the figure, from above the test plate 10 through the upward-facing bottom of the teflon cup 22.

FIG. 4 further shows that, placed in one of the wells 12 of the frame plate 11 in this embodiment of the test plate 10, there is a neutral density filter 21 cut from a quartz plate, which is also locked in position on the bottom of the well 12 of the frame plate 11 by a locking spring ring 25. As an optical measurement of the filter 21 is performed through the filter, the bottom of the well 12 is provided with an aperture 14 for this purpose. Thus, an optical measurement can be performed in the directions indicated by the arrows shown in the figure, either from above or from below.

ADDITIONAL REMARKS

Optical measurements of the test plate described above can be performed e.g. under computer control so that, using the test plate, the device to be tested performs the desired checks automatically. In this case, computer control corresponds to the various steps needed in manual measurements, so it has no inventive significance in itself. It is obvious to the person skilled in the art that different embodiments of the invention may be varied within the scope of the claims presented below.

LIST OF REFERENCE NUMERALS 10 test plate
11 frame plate
12 well
13 cover plate
14 aperture
20 sample unit (cup)
21 filter sample unit
22 cup part
23 cover
24 powder
25 locking spring ring

What is claimed is:

1. Method for checking the operation of an optical measuring device, such as a laboratory instrument used in biochemistry, by using a checking device (10), such as a test plate, according to the method a test plate (10) is formed for the measuring device by placing in the wells (12) of a plate (11) corresponding to a micro titer plate different sample units (20, 21) whose verified measured values are known, the checking of the operation of the measuring device is accomplished by measuring the sample units (20, 21) placed in the wells (12) of the aforesaid plate (11) and comparing the measurement results obtained to the previously known measured values verified by means of a reference device, characterized in that an individual test plate (10) is formed for each measuring device, in the aforesaid test plate (10), sample units (20, 21) are placed by means of which the reliability of the measuring device can be tested by the measuring methods used by the measuring device, such as e.g. fluorescence, luminescence and photometric determinations, the aforesaid test plate (10) is marked with an identifier, such as e.g. a serial number, identifying the measuring device, and that the user of the aforesaid measuring device checks the operation of the measuring device by performing a measurement on the device-specific individual test plate (10) and comparing the measurement results obtained to previously known measurement values for the test plate, verified by a reference device.

2. Checking device (10), such as a test plate, for checking the operation of an optical measuring device, such as a laboratory instrument used in biochemistry, at least one previously verified measurement value for said device being known, said checking device (10) comprising a frame plate (11), which preferably is the size of a micro titer plate, the frame plate (11) is provided with wells (12) or similar mounting points for sample units (20, 21), and the sample units (20, 21) are solid bodies that can be fixedly mounted in the wells (12) or similar mounting points of the frame plate (11), characterized in that a sample unit (20) to be mounted in a well (12) in the frame plate (11) of the said checking device (10) is a cup (22), inside which sample material (24) is placed, and that the sample unit (20) comprises a cover (23) for closing the cup (22).

3. Checking device (10) according to claim 2, characterized in that the cup (22) of the sample unit (20) of said checking device (10) is made of a material as neutral as possible in regard of measurement, such as teflon plastic or a ceramic material, the cup (22) contains a fluorescent substance (24), preferably in powdery form, the cover (23) of the cup (22) is made of a material as stable as possible, such as black anodized aluminum, the cup (22) is so placed in the frame plate (11) of the checking device (10) that optical measurement takes place through the bottom of the cup, and that the cup (22) is placed in the frame plate (11) of the checking device (10) with its bottom upward when optical measurement is performed from above the frame plate through the bottom of the cup.

4. Checking device (10) according to claim 2, characterized in that the sample material (24) in the cup (22) of the sample unit (20) of the aforesaid checking device (10) is fluorescent powder as such or diluted with non-fluorescent powder.

5. Checking device (10) according to claim 2, characterized in that the sample material (24) in the cup (22) of the sample unit (20) of said checking device (10) consists of fluorescent powder to which a liquid producing luminescence or corresponding material has been added.

6. Checking device (10) according to claim 2, characterized in that the sample unit (21) to be mounted in a well (12) in the frame plate (11) of said checking device (10) is an optical filter, which preferably consists of a metal-coated quartz plate.

7. Checking device (10) according to claim 2, characterized in that the frame plate (11) of said checking device (10) is preferably made of transparent or black plastic, that the frame plate (11) contains preferably 96 wells of circular cross-section, and that the sample units (20, 21) fitted to the wells (12) and fixedly mounted in them have a corresponding round shape.

8. Checking device according to claim 2, characterized in that, placed in the wells (12) of the frame plate (11) of said checking device (10) are sample units (20, 21) used for the checking of two or more measuring methods, e.g. fluorescence and/or luminescence and/or photometric measuring units.

9. Checking device according to claim 2, characterized in that one or more wells (12) in the frame plate (11) of said checking device have an aperture (14) in their bottom so that a through hole exists in the frame plate in the region of the aperture, at least one cup (22) of the sample unit (20) is placed with the cover (23) upward in a well (12) with an aperture (14) in its bottom, thus permitting an optical measurement to be performed through the bottom of the cup from below the frame plate (11) via the aforesaid aperture, at least one optical filter of a sample unit (21) is placed in a well (12) with an aperture (14) in its bottom, permitting an optical measurement penetrating said filter to be performed from either side of the frame plate (11).

10. Checking device (10) according to claim 2, characterized in that the sample unit (20), which comprises a sample cup (22) or sample unit (21) which is an optical filter, is placed on the bottom of a well (12) in the frame plate (11) of the checking device (10), and that, to lock the sample units (20, 21) in place, the well (12) of the frame plate (11) is provided with a locking ring, such as a spring ring, placed above the sample unit.

* * * * *